(12) United States Patent
Fetzer

(10) Patent No.: US 8,357,087 B2
(45) Date of Patent: *Jan. 22, 2013

(54) PUSH-BUTTON ACTIVATED GRASPER FOR SURGICAL RETRACTOR

(76) Inventor: Peter Edward Fetzer, Oehningen-Wangen (DE)

( * ) Notice: Subject to any disclaimer, the term of this patent is extended or adjusted under 35 U.S.C. 154(b) by 708 days.

This patent is subject to a terminal disclaimer.

(21) Appl. No.: 12/319,196

(22) Filed: Jan. 2, 2009

(65) Prior Publication Data

US 2009/0124861 A1 May 14, 2009

Related U.S. Application Data

(63) Continuation of application No. 11/052,543, filed on Feb. 7, 2005, now Pat. No. 7,473,223.

(51) Int. Cl.
A61B 1/32 (2006.01)

(52) U.S. Cl. ........................................................ 600/213

(58) Field of Classification Search ................ 600/213, 600/217, 226–227, 234, 237; 292/4–13, 292/22, 51, 112, 160, 172, 142, 199, 279–280; 24/453

See application file for complete search history.

(56) References Cited

U.S. PATENT DOCUMENTS

| | | | | | |
|---|---|---|---|---|---|
| 659,425 | A | * | 10/1900 | White | 54/30 |
| 741,014 | A | * | 10/1903 | Covert | 24/600.8 |
| 1,062,653 | A | * | 5/1913 | Koons | 24/600.8 |
| 1,228,513 | A | * | 6/1917 | Anderson | 24/600.8 |
| 1,476,254 | A | * | 12/1923 | Jacobsky | 292/332 |
| 1,521,811 | A | * | 1/1925 | Hartbauer | 24/600.8 |
| 1,546,208 | A | * | 7/1925 | Cunningham | 294/82.2 |
| 1,576,197 | A | * | 3/1926 | Kuffel et al. | 294/82.19 |
| 1,583,347 | A | * | 5/1926 | Frischknecht | 24/600.8 |
| 1,598,684 | A | * | 9/1926 | Jensen | 24/600.8 |
| 1,626,866 | A | * | 5/1927 | Neilson | 294/82.2 |
| 1,679,902 | A | * | 8/1928 | Helwig | 24/600.8 |
| 1,687,006 | A | * | 10/1928 | Cornelius | 294/82.2 |
| 1,879,168 | A | * | 9/1932 | Freysinger | 24/600.1 |
| 2,595,450 | A | * | 5/1952 | Coffing | 294/82.33 |
| 2,939,734 | A | * | 6/1960 | Claud-Mantle | 292/64 |
| 3,756,088 | A | * | 9/1973 | Inoue | 74/89.17 |
| 3,811,720 | A | * | 5/1974 | Epstein | 294/82.34 |
| 4,064,873 | A | * | 12/1977 | Swenson | 600/215 |
| 4,263,899 | A | * | 4/1981 | Burgin | 600/213 |
| 4,379,579 | A | * | 4/1983 | Mahan et al. | 294/82.36 |
| 4,401,334 | A | * | 8/1983 | Kraeling, Jr. | 294/82.36 |
| 4,471,511 | A | * | 9/1984 | Phipps | 294/82.33 |
| 4,613,180 | A | * | 9/1986 | Pope | 294/82.34 |

(Continued)

FOREIGN PATENT DOCUMENTS

WO     WO 03/064788 A3     7/2003

*Primary Examiner* — Cris L Rodriguez
*Assistant Examiner* — Hao D Mai
(74) *Attorney, Agent, or Firm* — McDermott Will & Emery LLP

(57) ABSTRACT

A grasper for a surgical retractor is provided. The grasper has a grasper body, a push-button activator and a holder to releasably retain a connector head of, for example, a retractor blade. The holder is configured to move from a first position, located at least partially in the opening to provide for selectively retaining the connector head in the opening, to a second position wherein the connector head may be removed. The push-button activator is operably connected to the holder to move the holder from the first position to the second position. In one embodiment the holder is gear driven by the activator.

10 Claims, 3 Drawing Sheets

U.S. PATENT DOCUMENTS

| | | | | |
|---|---|---|---|---|
| 4,867,404 A * | 9/1989 | Harrington et al. | | 606/46 |
| 5,110,301 A * | 5/1992 | Inoue et al. | | 439/310 |
| 5,297,321 A | 3/1994 | Murai | | |
| 5,836,563 A * | 11/1998 | Hsin-Yung | | 248/316.4 |
| 5,893,831 A * | 4/1999 | Koros et al. | | 600/232 |
| 5,902,233 A * | 5/1999 | Farley et al. | | 600/213 |
| 5,988,709 A * | 11/1999 | Lee et al. | | 292/199 |
| 6,042,540 A * | 3/2000 | Johnston et al. | | 600/213 |
| 6,050,115 A * | 4/2000 | Schroter et al. | | 70/107 |
| 6,070,308 A * | 6/2000 | Rohlf | | 24/600.8 |
| 6,113,044 A * | 9/2000 | Stratman | | 248/220.42 |
| 6,325,811 B1 | 12/2001 | Messerly | | |
| 6,360,083 B1 * | 3/2002 | Fan | | 455/90.1 |
| 6,408,493 B1 * | 6/2002 | Yurman et al. | | 24/600.4 |
| 6,449,991 B1 * | 9/2002 | Hogan | | 70/57.1 |
| 6,572,540 B2 * | 6/2003 | Dobrovolny | | 600/226 |
| 6,645,141 B1 | 11/2003 | Phillips et al. | | |
| 6,729,205 B2 * | 5/2004 | Phillips | | 74/577 M |
| 6,733,444 B2 * | 5/2004 | Phillips | | 600/213 |
| 6,736,775 B2 * | 5/2004 | Phillips | | 600/234 |
| 6,790,177 B2 | 9/2004 | Phillips et al. | | |
| 6,860,850 B2 * | 3/2005 | Phillips et al. | | 600/227 |
| 6,887,197 B2 * | 5/2005 | Phillips | | 600/213 |
| 6,887,198 B2 | 5/2005 | Phillips et al. | | |
| 6,976,969 B2 | 12/2005 | Messerly | | |
| 7,147,599 B2 | 12/2006 | Phillips et al. | | |
| 7,191,683 B2 | 3/2007 | Phillips et al. | | |
| 7,473,223 B2 * | 1/2009 | Fetzer | | 600/213 |
| 7,569,014 B2 * | 8/2009 | Bass et al. | | 600/213 |
| 7,588,537 B2 * | 9/2009 | Bass | | 600/234 |
| 2005/0272981 A1 * | 12/2005 | Bjork et al. | | 600/227 |
| 2007/0055109 A1 * | 3/2007 | Bass et al. | | 600/234 |
| 2007/0055110 A1 * | 3/2007 | Bass | | 600/234 |
| 2007/0283538 A1 * | 12/2007 | Ito et al. | | 24/269 |

* cited by examiner

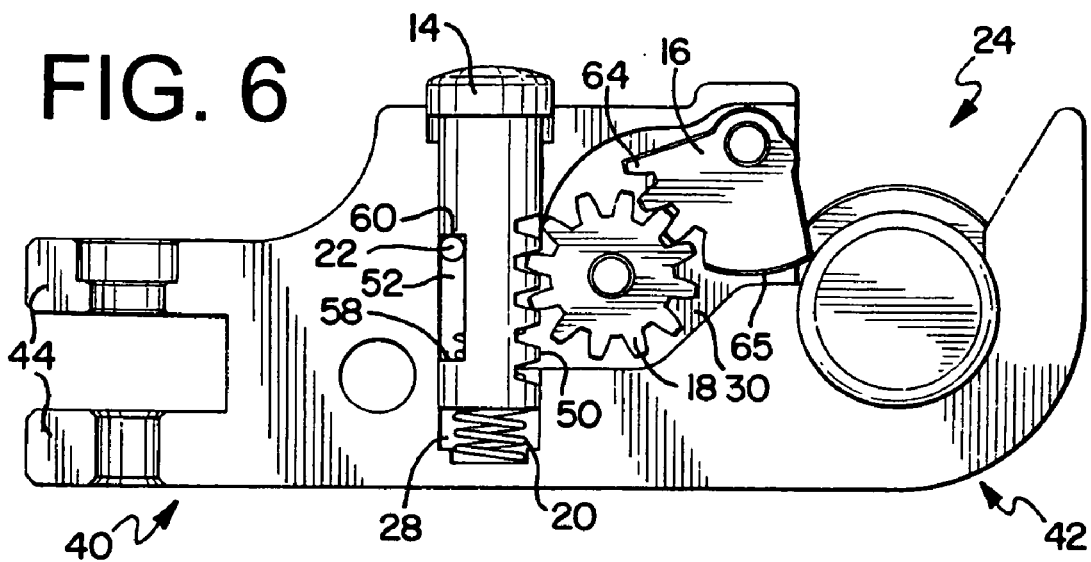
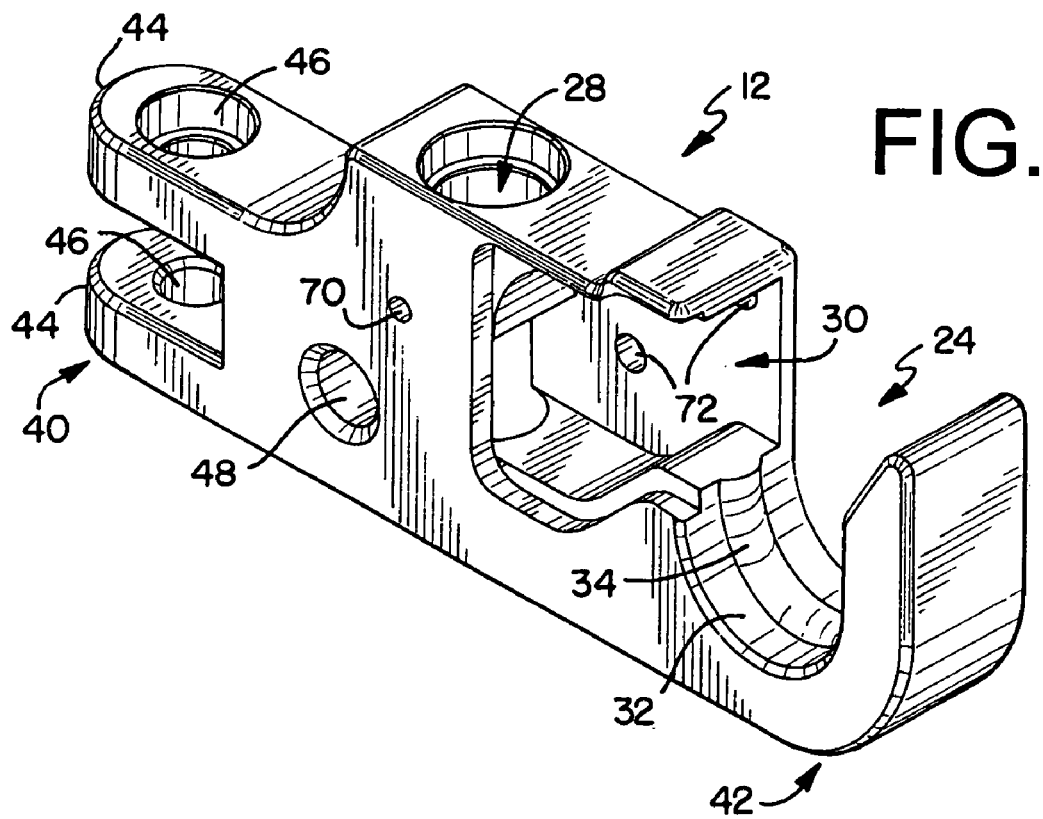

PUSH-BUTTON ACTIVATED GRASPER FOR SURGICAL RETRACTOR

CROSS-REFERENCE TO RELATED APPLICATIONS

This application is a continuation of U.S. application Ser. No. 11/052,543, filed Feb. 7, 2005, now U.S. Pat. No. 7,473,223 which is expressly incorporated herein by reference.

FEDERALLY SPONSORED RESEARCH OR DEVELOPMENT

Not Applicable.

TECHNICAL FIELD

This invention relates generally to a grasper for a retractor, and more particularly, to a push-button activated grasper for a surgical retractor.

BACKGROUND OF THE INVENTION

Surgical retractors and graspers therefor are well known in the art. While such graspers according to the prior art provide a number of advantageous features, they nevertheless have certain limitations. The present invention seeks to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention generally provides a side-loading push-button activated grasper for a surgical retractor. The grasper has a grasper body, an activator, and a holder to releasably retain a connector head of, for example, a retractor blade. The holder is configured to move from a first position, located at least partially in the opening to provide for retaining the connector head in the opening, to a second position wherein the connector head may be removed.

According to one embodiment, the grasper body has a first surface defining an opening to accept a connector head, and a gear-actuated holder connected to the body and configured to move from a first position to a second position.

According to another embodiment, a push-button activator is provided and is seated partially within the grasper body and operably connected to the gear-actuated holder. The push-button activator has a gear member to actuate the holder from the first position to the second position. In one embodiment, the activator has a gear track with engaging mating members to actuate the holder.

According to another embodiment, the push-button activator has a longitudinal axis that is transverse to a longitudinal axis of the grasper body, and the push-button activator travels about its longitudinal axis. Further, the push-button activator moves from a normal position to an activated position, thereby manipulating the holder from the first position to the second position.

According to another embodiment, a spring is provided within the grasper body. The spring engages the push-button activator to bias the push-button activator to the normal position.

According to another embodiment, an actuating member is provided between the push-button activator and the holder. The actuating member engages both the gear track on the push-button activator and the holder to translate motion from the push-button activator to the holder. In one embodiment the actuating member is a gear that rotates about a shaft located in a cavity within the grasper body.

According to another embodiment, the holder is rotatedly connected to the grasper body. In one embodiment the holder has at least one engaging member adapted to be driven by the gear track on the push-button activator.

According to yet another embodiment, a rib extends from the first surface of the grasper body into the opening. In another embodiment, another rib extends from the holder and is dimensioned to cooperate with the rib extending from the first surface of the grasper body. The ribs are adapted to mate with a groove in the connector head.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 6 is a partial cut-away front elevation view of the grasper of FIG. 5 in the actuated position; and, FIG. 7 is a perspective view of the grasper body.

DETAILED DESCRIPTION

Figure 1:
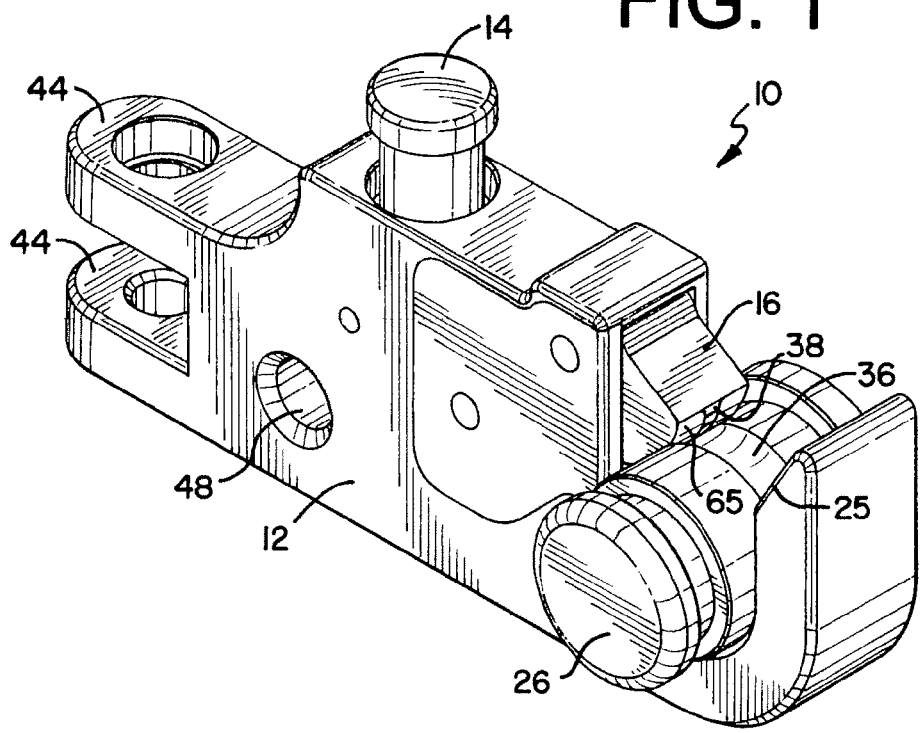
FIG. 1 is a perspective view of one embodiment of a grasper for a surgical retractor, the grasper being provided in the normal position.

While this invention is susceptible of embodiments in many different forms, there are shown in the drawings and will herein be described in detail, preferred embodiments of the invention with the understanding that the present disclosures are to be considered as exemplifications of the principles of the invention and are not intended to limit the broad aspects of the invention to the embodiments illustrated.

Figure 2:
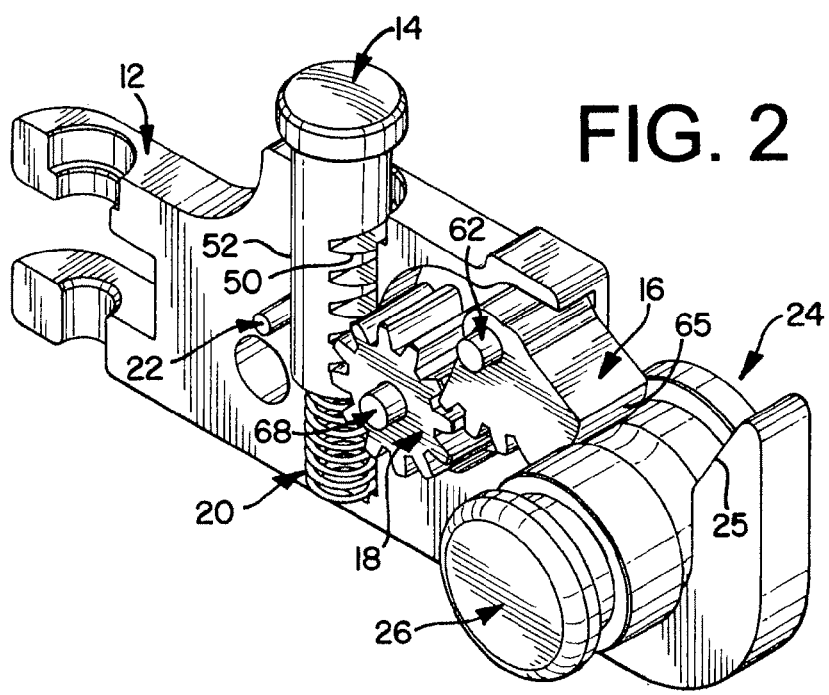
FIG. 2 is a partial cut-away perspective view of the grasper of FIG. 1.
Figure 3:
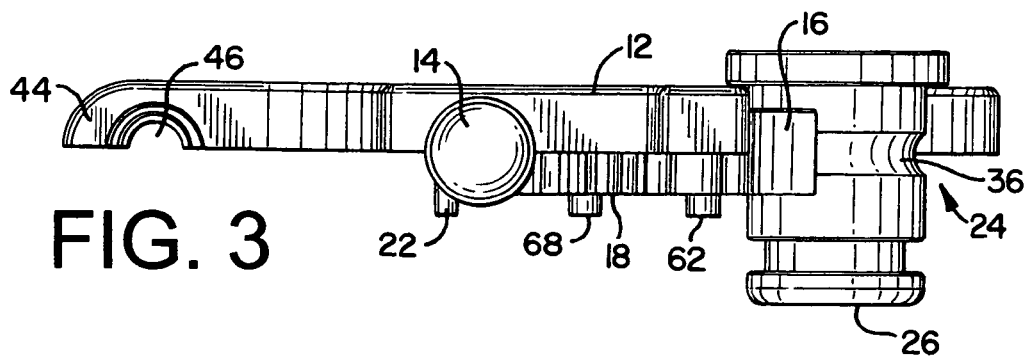
FIG. 3 is a partial cut-away top plan view of the grasper of FIG. 1.

Referring now in detail to the Figures, and specifically to FIGS. 1 and 2, there is shown an embodiment of a grasper 10 for a retractor assembly. In one embodiment, the grasper 10 is push-button activated. In general, the grasper 10 comprises a grasper body 12, an activator 14, a holder 16, an actuating member 18, a spring 20 and a pin 22. The grasper body 12 has an opening 24 which is configured to accept a connector head 26 for a retractor blade or other retractor component (not shown). Further, the holder 16 is configured to move from a first or normal position (generally shown in FIGS. 1-4) to a second or actuated position (generally shown in FIGS. 5 and 6). In the first position, a portion of the holder 16 is located at least partially in the opening 24 to provide for retaining the connector head 26 in a seated position in the opening 24 of the grasper 10. Upon actuation to the second position, the holder 16 is configured to allow the connector head 26 to be removed from the grasper 10.

As shown in FIG. 7, in one embodiment the grasper body 12 comprises a unitary component having a first cavity 28 and a second cavity 30. Referring to assembled grasper 10 in FIGS. 4 and 6, the first cavity 28 houses the spring 20, the pin 22 and a portion of the activator 14, and the second cavity 30 houses the actuating member 18 and a portion of the holder 16. In one embodiment the first cavity 28 is joined to the second cavity 30.

The grasper body 12 also has an opening 24 defined by a first surface 32 thereof. The opening 24 is generally U-shaped and has an arcuate portion to mate with the cylindrical or arcuate shape of the connector head 26. Further, the opening 24 provides a side-loading socket for accepting the connector head 26 adjacent the first surface 32 of the grasper body 12. Accordingly, the opening 24 is dimensioned to receive, retain and release the connector head 26. To assist in accomplishing these features, a rib 34 extends from the first surface 32 of the grasper body 12 and into the opening 24 thereof. The rib 34 generally mates with a corresponding groove 36 on the connector head 26 when the connector head 26 is side-inserted into the opening 24. In one embodiment, such as shown in FIG. 1, the holder 16 also has a similar rib 38 extending from its outer surface. The rib 38 of the holder 16 is dimensioned to cooperate with the rib 34 extending from the first surface 32 of the grasper body 12 to mate with the corresponding groove 36 on the connector head 26 and thereby seat the connector head 26 in the opening 24 of the grasper body 12. The ribs 34 and 38 may extend any desired length about their respective extending surfaces. Further, by their physical protrusion into the opening 24 of the grasper body 12, one of ordinary skill in the art would readily understand that the ribs 34 and 36, both independently and collectively, operate to prohibit top loading of the connector head. In an alternate embodiment, however, the holder 16 does not have a rib 34, but rather only has a cam surface 65. The entrance to the opening 24 has a chamfered or beveled portion 25 as a lead-in to assist in seating the connector head 26 in the opening 24 of the grasper body 12.

The grasper body 12 has a proximal end 40 and a distal end 42, and a longitudinal axis that extends generally from the proximal end 40 to the distal end 42. In one embodiment the opening 24 is provided generally adjacent the distal end 42 of the grasper body 12, and a pair of attachment arms 44 are provided at the proximal end 40 of the grasper body 12. The attachment arms 44 provide a means for connecting the grasper 10 to a retractor arm (not shown). Further, in this embodiment the arms 44 have openings 46 into which a bolt or other fastener is inserted to hingedly connect the grasper 10 to the retractor. As such, the grasper 10 may be rotated about the fastener arm to allow the grasper 10 to be positioned closer to the surgical site. Additionally, this embodiment of the grasper body 12 has a suture hole 48 to permit the retractor arms to be sutured in place and thereby to assist in preventing movement of the retractor after the retractor is positioned by the operator.

Figure 4:
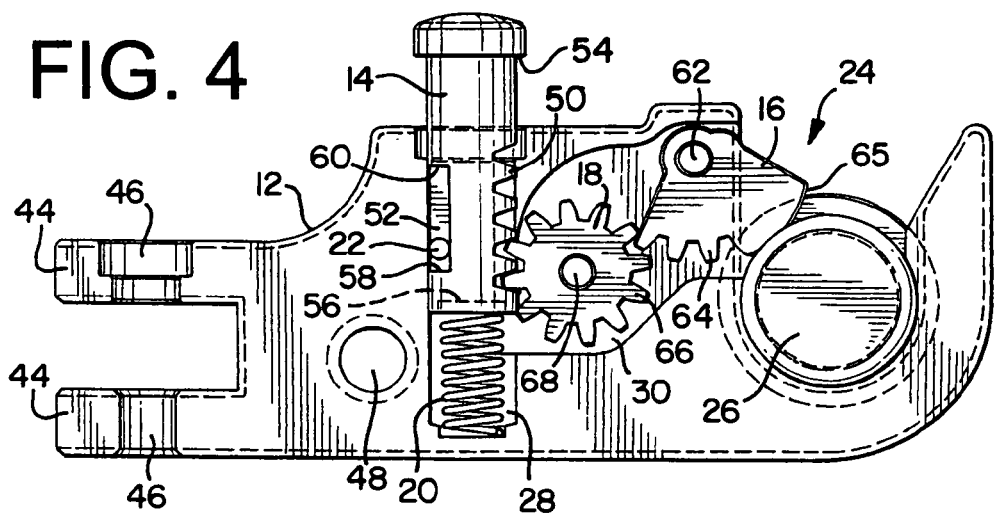
FIG. 4 is a partial cut-away front elevation view of the grasper of FIG. 1.
Figure 5:
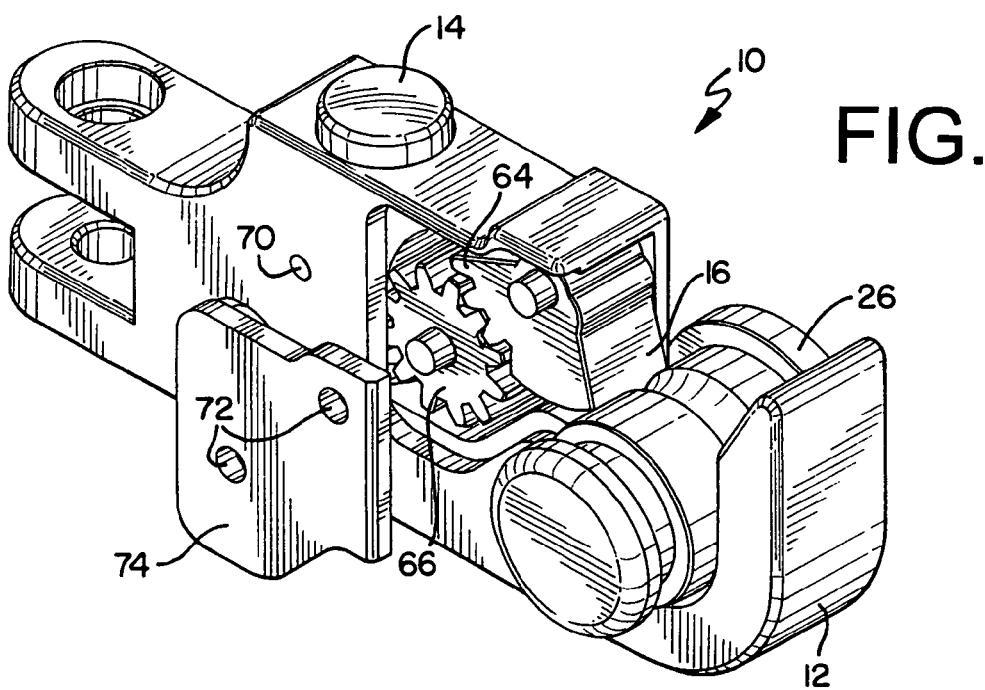
FIG. 5 is a perspective view of the grasper of FIG. 1 in an actuated position and with a portion of the side body panel removed.

As explained above, the first cavity 28 of the grasper body 12 houses the spring 20, the pin 22 and a portion of the activator 14. In a preferred embodiment the activator 14 is a push-button member 14 that manipulates the holder 16 to provide for selectively retaining and releasing the connector head 26. In this embodiment the spring 20 is generally a compression spring. A first end of the spring 20 is provided against the bottom of the first cavity 28, and a second end of the spring 20 is provided against the push button activator 14 to exert an upward force on the push-button activator 14. As shown in FIG. 4, the bottom of the push-button activator 14 has a bore 56 to position and retain the second end of the spring 20 therein.

In general, the push-button activator 14 is at least partially seated within the grasper body 12, extends transversely from the grasper body 12, and is operable connected to the holder 16 to move the holder 16 from the normal position to the actuated position. In one embodiment, the push-button activator 14 is a generally cylindrical component having a gear member to actuate the holder 16, an opposing recess 52 on its outer surface, a shoulder 54 at its first end and a bore 56 at its second end. In a preferred embodiment the gear member is a gear track 50. Further, the activator 14 has a longitudinal axis that extends from its first end to its second end, and it is understood that in this embodiment the activator 14 travels about its longitudinal axis. In its assembled form, the longitudinal axis of the activator 14 is transverse to a longitudinal axis of the grasper body 12. As best shown in FIGS. 4 and 6, the recess 52 has a first shoulder 58 and a second shoulder 60, and the pin 22 in the first cavity 28 of the grasper body 12 operates as both a guide and a stop for the push-button activator 14. In the normal position, i.e., FIG. 4, the spring 20 engages the activator 14 by exerting an upward force on the activator 14 to bias the activator 14 to the normal position. The pin 22, however, engages the first shoulder 58 of the recess 52 and operates as a stop to prevent additional upward movement of the activator 14. When the operator actuates the grasper 10 by pushing downward on the activator 14 to overcome the force of the spring 20, see FIG. 6, the activator 14 is pushed further into the first cavity 28 until either the second shoulder 60 of the activator recess 52 engages the pin 22, or the shoulder 54 of the activator 14 bottoms out on a counter-bore of the first cavity 28. This is referred to as the actuated position. As such, the pin 22 also operates as a cam for the activator 14, and the surfaces of the recess 52 operate as the cam follower. In a preferred embodiment, the pin 22 extends from one side of the grasper body 12 to the opposing side thereof.

As best shown in FIGS. 4 and 6, in one embodiment the gear track 50 of the actuator opposes the recess 52. In this embodiment, the gear track 50 of the activator 14 generally comprises a plurality of gear teeth which are adapted to engage mating members to actuate the holder 16. In a preferred embodiment the gear track 50 of the activator 14 is linear, however, it is understood that any geometry of a gear, pulley, rack, pinion, or other drive mechanism is possible without departing from the scope of the present invention.

In one embodiment the holder 16 is rotatedly connected to the grasper body 12 within the second cavity 30 thereof. In this embodiment, a first shaft 62 extends from one side of the grasper body 12 to the opposing side of the grasper body 12 to rotatedly support the holder 16. In a preferred embodiment the holder 16 has a plurality of engaging members 64, such as gear teeth, extending therefrom which are adapted to be driven by the activator 14. As explained above, in one embodiment the holder 16 also has an outer surface that may operate as a cam surface 65, and a rib 38 extending from its outer surface. The outer surface 65 generally has an arcuate shape, and in one embodiment the outer surface 65 has a convex shape thereto. Further, if provided, the rib 38 of the holder 16 is dimensioned to cooperate with the rib 34 extending from the first surface 32 of the grasper body 12 to mate with the corresponding groove 36 on the connector head 26 and thereby seat the connector head 26 in the opening 24 of the grasper body 12.

In addition, an actuating member 18 may be provided to assist in translating motion from the activator 14 to the holder 16. The actuating member 18 is generally positioned in the second cavity 30 and between the activator 14 and the holder 16. In the embodiment illustrated, the actuating member 18 is a gear 66 that rotates about a second shaft 68 extending between the opposing sides of the grasper body 12. The actuating member 18 engages both the gear track 50 on the activator 14 and the engaging members 64 on the holder 16. Thus, the holder 16 is positively driven by actuation of the activator 14. In such an embodiment, as with other possible embodiments, the holder 16 is defined as being gear actuated.

To assemble the embodiment of the grasper 10 of FIG. 1, the spring 20 is inserted into the first cavity 28 of the grasper body 12 such that the first end of the spring 20 is positioned against the bottom of the first cavity 28. The activator 14 is then inserted into the first cavity 28 and the second end of the spring 20 is positioned in the bore 56 at the second end of the activator 14. Next, the pin 22 is inserted through an aperture 70 in the sidewall of the grasper body 12 and positioned against or adjacent the cam follower surface of the recess 52 of the activator 14. Thus, the pin 22 operates to moveably secure the activator 14 within the first cavity 28 of the grasper body 12.

The first and second shafts 62 and 68 are then inserted into the respective retaining apertures 72 in the side wall of the grasper body 12. The actuating member 18 is fitted onto the second shaft 68, such that the engaging members of the actuator 18 engage the gear track 50 of the activator 14. Similarly, the holder 16 is fitted onto the first shaft 62 such that the engaging members 64 of the holder 64 engage the engaging members of the actuating member 18. After the actuating member 18 and the holder 16 are assembled in place, the cap 74 is positioned on the opposing ends of the first and second shafts 62 and 68 and closes off the side of the second cavity 30, thereby securing the actuating member 18 and the holder 16 in axial place. Each of the shafts and the cap 74 are then laser welded to the grasper body 12 and the entire grasper 10 is surface ground and polished.

In the assembled embodiment, the normal state of the grasper 10 has the holder 16 extending at least partially in the opening 24 of the grasper body 12. In such a position a connector head 26 would be retained in the opening 24 and the ribs 34 and 38 of the holder 16 and the grasper body 12 would cooperate to mate with the corresponding groove 36 on the connector head 26 and thereby seat the connector head 26 in the opening 24 of the grasper body 12. To release the connector head 26, an operator would push down on the push-button activator 14. As the push-button activator 14 is activated, the gear track 50 drives the actuating member gear 18 which in turn drives the engaging members of the holder 16 to rotate the holder 16 into the second position such that the connector head 26 can be removed from the grasper 10.

In a preferred embodiment each of the components of the grasper 10 are made of a material that is easily sanitized and provides good wear characteristics, such as stainless steel or titanium, however it is understood by one of ordinary skill in the art that the components of the grasper 10 may be made of any rigid material.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Additionally, the terms "first," "second," "third," and "fourth" as used herein are intended for illustrative purposes only and do not limit the embodiments in any way. Further, the term "plurality" as used herein indicates any number greater than one, either disjunctively or conjunctively, as necessary, up to an infinite number.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying Claims.

What is claimed is:

1. A grasper for a surgical retractor, the grasper comprising:
   a grasper body having a first surface defining a surgical instrument connector head opening;
   a holder configured to move from a first position to a second position, the holder selectively retaining the surgical instrument connector head in the opening in the first position;
   a push-button activator operably connected to the holder, the push-button activator transitionable from a normal position to an activated position to assist in manipulating the holder from the first position to the second position, the push-button activator having a longitudinal axis that is transverse to a longitudinal axis of the grasper body, the push-button activator traveling only in its longitudinal axis; and,
   a spring within the grasper body and directly engaging the push-button activator to bias the push-button activator to the normal position, wherein the push-button activator has a gear track, the gear track engaging mating members to actuate the holder.

2. The grasper of claim 1, wherein the holder is rotatedly connected to the grasper body.

3. The grasper of claim 1, wherein the push-button activator is at least partially seated within the grasper body.

4. The grasper of claim 1, wherein the holder has at least one engaging member adapted to be driven by the gear track on the push-button activator.

5. The grasper of claim 1, further comprising an actuating member between the push-button activator and the holder, the actuating member engaging both the gear track on the push-button activator and the holder to translate motion from the push-button activator to the holder.

6. The grasper of claim 5, wherein the actuating member is a gear that rotates about a shaft located in a cavity within the grasper body.

7. The grasper of claim 1, further comprising a rib extending from the first surface of the grasper body into the opening.

8. The grasper of claim 7, further comprising a rib extending from the holder and dimensioned to cooperate with the rib extending from the first surface of the grasper body.

9. A grasper for a surgical retractor, the grasper comprising:
   a grasper body having a first surface defining an opening to accept a surgical instrument connector head;
   a holder rotatably connected to the grasper body and configured to move from a first position to a second position, the first position being at least partially in the opening;
   an activator transversely extending from the grasper body and operably connected to the holder, wherein the activator travels only in its longitudinal axis to assist in transitioning the holder from the first position to the second position, and wherein the holder is gear driven by the activator.

10. The grasper of claim 9, wherein the activator is a push-button activator having a longitudinal axis transverse to a longitudinal axis of the grasper body.

* * * * *